United States Patent
Miller

(10) Patent No.: US 10,857,151 B1
(45) Date of Patent: Dec. 8, 2020

(54) TREATMENT OF FEMALE GENITAL SCHISTOSOMIASIS

(71) Applicant: William Miller, Melbourne, FL (US)

(72) Inventor: William Miller, Melbourne, FL (US)

(73) Assignee: Villya LLC, Melbourne, FL (US)

( * ) Notice: Subject to any disclaimer, the term of this patent is extended or adjusted under 35 U.S.C. 154(b) by 0 days.

(21) Appl. No.: 16/797,206

(22) Filed: Feb. 21, 2020

(51) Int. Cl.
*A61K 31/5025* (2006.01)
*A61K 9/06* (2006.01)
*A61K 9/02* (2006.01)
*A61P 33/12* (2006.01)
*A61K 9/00* (2006.01)

(52) U.S. Cl.
CPC ........ *A61K 31/5025* (2013.01); *A61K 9/0053* (2013.01); *A61K 9/02* (2013.01); *A61K 9/06* (2013.01); *A61P 33/12* (2018.01)

(58) Field of Classification Search
None
See application file for complete search history.

(56) References Cited

U.S. PATENT DOCUMENTS

| | | | |
|---|---|---|---|
| 6,416,779 B1 * | 7/2002 | D'Augustine | A61K 9/0034 424/430 |
| 8,461,115 B2 | 6/2013 | Uttenthal | |
| 8,840,869 B2 | 9/2014 | Friedman et al. | |
| 9,333,329 B2 | 5/2016 | Ziv | |
| 10,201,576 B2 | 2/2019 | Rishi | |
| 10,350,042 B2 | 7/2019 | Schuman et al. | |
| 10,391,134 B2 | 8/2019 | Meuwly et al. | |
| 10,555,900 B2 | 2/2020 | Podolski et al. | |

OTHER PUBLICATIONS

Female Genital Schistosomiasis—A Pocket Atlas for Clinical Health Care Professionals World Health Organization (2015) (Year: 2015).*
Treatment of FGS with Praziquantel at https://clinicaltrials.gov/ct2/show/ NCT04115072 at https://clinicaltrials.gov/ ct2/show/ NCT04115072 (retrieved from the internet Jul. 8, 2020) (Year: 2019).*
Alexander et al. in Fertility and Sterility, 82(1) 1-12 (2004) (Year: 2004).*
Zonolla et al. in European Journal of Pharmaceutics and Biopharmaceutics 127, 19-28 (2018) (Year: 2018).*
Bribeche et al. in Clinical and Experimental Dermatology 39, 448-453 (2014) (Year: 2014).*
Goodman and Gilman's The Pharmacological Basis of Therapeutics (Tenth Edition (2001), McGraw Hill, Chapter I, pp. 3-29 (Year: 2001).*
El-Feky et al. in Antimicrobial Agents and Chemotherapy 59(6), 3501-3508 (2015) (Year: 2015).*
"Female Genital Schistosomiasis, A Pocket Atlas for clinical Health-Care Professionals," WHO Library Cataloguing-in-Publication, 2015Data.
Hotez et al. "Female genital schistosomiasis and HIV/AIDS: Reversing the neglect of girls and women" PLOS Neglected Tropical Diseases, 13(4):e0007025 (2019).
Abla et al. "Evaluation of the pharmacokinetic-pharmacodynamic relationship of praziquantel in the Schistosoma mansoni mouse model" PLOS Neglected Tropical Diseases, 11(9):e0005942 (2017).

* cited by examiner

*Primary Examiner* — Dennis Heyer
(74) *Attorney, Agent, or Firm* — Banner & Witcoff, Ltd.

(57) ABSTRACT

Formulations of praziquantel are used to locally treat female genital schistosomiasis. The formulations can be applied to the upper or lower female genital tract, depending on the location of the infection. Thick or viscous formulations can be used advantageously in the vagina. Solutions of active ingredient can be instilled in the uterus.

29 Claims, No Drawings

US 10,857,151 B1

TREATMENT OF FEMALE GENITAL SCHISTOSOMIASIS

TECHNICAL FIELD OF THE INVENTION

This invention is related to the area of tropical diseases. In particular, it relates to female genital parasitic infection.

BACKGROUND OF THE INVENTION

Schistosomiasis (also known as bilharziasis) is a worm infection endemic to tropical areas. Human schistosomiasis is widespread in both rural and urban areas of the world. The worms infect people via skin contact with infested fresh water. The worms lay eggs in the host human, some of which reside in organs, such as the cervix, uterus, fallopian tubes, or lower female genital tract, and some of which are excreted. The eggs, which stimulate a the host inflammatory response and increased vascularization, produce lesions.

Female genital schistosomiasis (FGS) is caused by schistosome eggs deposited in genital tissues. According to the World Health Organization, FGS may be the most common gynecological condition in schistosomiasis-endemic areas. People with FGS are far more susceptible to HIV and human papillomavirus infections, which are associated with increased mortality. FGS may also result in infertility.

Schistosomiasis is often treated with oral praziquantel including in mass drug administration programs by public health authorities. While such treatment successfully treats systemic infection by worms, it is far less successful in treating FGS caused by adult schistosomiasis worms living on the other side of the tissue explicitly in the biome of the female reproductive system. There is a continuing need in the art to develop improved means for treating FGS.

SUMMARY OF THE INVENTION

According to one aspect of the invention a method is provided for treating genital schistomiasis in a female patient. An effective dose of praziquantel is inserted and deposited into the vaginal cavity of the female patient. The amount of adult worms is thereby decreased.

According to another aspect of the invention a method is provided for treating uterine schistosomiasis or uterine fibroids related to schistosomiasis in a female patient. An intrauterine catheter is inserted into the uterus and an effective dose of an aqueous solution of praziquantel is delivered via the intrauterine catheter to the uterus. The amount of adult *schistosoma* worms, *schistosoma* eggs, or fibroids related to schistosomiasis is thereby decreased.

Another aspect of the invention is a pharmaceutical composition for treating female genital schistosomiasis. The pharmaceutical composition comprises praziquantel in a water soluble vehicle.

Still another aspect of the invention is a unit dosage form of praziquantel. The unit dosage from may be 400-1000 mg praziquantel per about 2.5 g vaginal vehicle, 800-1500 mg praziquantel per about 5 g vaginal vehicle, 100-500 mg praziquantel per about 1.25 g vaginal vehicle, or 800-1500 mg praziquantel per about 20 ml normal saline uterine vehicle.

Yet another aspect of the invention is a kit for locally treating female genital tissue infected with schistosomes. The kit comprises a vaginal applicator and praziquantel.

A further aspect of the invention is a kit for locally treating uterine tissue infected with schistosomes. The kit comprises an intrauterine catheter, normal saline, and praziquantel.

A vaginal applicator is provided as another aspect of the invention. The vaginal applicator comprises a reservoir and an expeller. The reservoir is preloaded with praziquantel and a water soluble vehicle. The expeller urges the praziquantel and the water soluble vehicle out of the reservoir and out of the vaginal applicator upon activation by a user.

These and other embodiments which will be apparent to those of skill in the art upon reading the specification provide the art with methods and tools for treating FGS or other parasitic worm infections of tissues.

DETAILED DESCRIPTION OF THE INVENTION

The inventor has developed an effective way to treat a widespread but underappreciated scourge of tropical medicine, female genital schistosomiasis. Local delivery of drug to the affected organs results in amelioration or cure where systemic delivery was ineffective.

The treatments and devices and kits described here can be used for treating tissue infected with worms or eggs of *Schistosoma* species parasites. The most common species involved in these infections are *Schistosoma haematobium*. The treatment leads to a reduction in the number of worms present in the treated part of the body, a reduction in lesions, and a reduction in symptoms. Typical symptoms which may be reduced include one or more of vaginal discharge, bloody discharge, bleeding after intercourse, genital itching and pain, burning sensation, pelvic pain, pain during intercourse (dyspareunia), bloody urine.

Body parts which may function as depositories of schistosome eggs include without limitation the cervix, vagina, vulva, uterus, and fallopian tubes. These may be associated with abortion or ectopic pregnancy, genital ulcers, tumors or swelling, infertility, involuntary urination, and bleeding.

FGS can be diagnosed in women and girls by clinical examination to observe characteristic lesions, typically on the cervix, fornices, and vaginal wall or by urine antigen (schistomsomiasis) cassette test. Observation can be improved by using assistive devices such as cameras and colposcopes. Additionally, samples can be obtained, such as mucosal or cell scrapings or brushings, and examined microscopically for observation of worms or eggs.

Oral treatment with praziquantel is highly successful for reducing and eliminating systemic, blood-borne infections. The treatment kills adult worms. Typically, a dose of 40 mg/kg of body weight is used as a single dose or 20 mg/kg 3× in 1 day. However, efficacy against worms in cavity tissue infection is far less.

Local treatment to the vagina or uterus, for example, will utilize a dosage that is appropriate for the size and age of the female subject. For a child with a minimum weight of 15 kg, a dose of 100-500 mg praziquantel, preferably 300 mg praziquantel in 1.25 g carrier may be used, for example. For an adult of greater than 70 kg, a dose of 400-1000 mg praziquantel, preferably 600 mg praziquantel in a 2.5 g of carrier may be used, for example. For a larger adult of greater than 100 kg, a dose of 800-1500 mg praziquantel, preferably 1200 mg praziquantel, can be used in 5 g of carrier.

The drug solution or formulation can be loaded by the user, the clinician, or pre-loaded by the manufacturer or formulator in a vaginal applicator. This may be, for example, a simple, single-use plastic applicator tube with a plunger as an expeller of the payload from the vaginal applicator. Other means of expelling may be used, such as a constricting mechanism to narrow the circumference of the applicator tube. Applicators may be multiple use and/or made of other materials not limited to glass, metal, or carbon fiber. Multiple use applicators can be cleaned and sterilized between uses.

In one embodiment the therapeutic formulation may be impregnated in a tampon which is then inserted into the vaginal canal. The tampon may be inserted by hand or with an applicator, as is known in the art.

A vaginal applicator should be inserted deep into the vaginal canal prior to activation of the plunger and expelling the contents of the applicator. This maximizes the anatomical coverage in the canal given the action of gravity to draw the expelled contents down the vaginal canal.

Treatment is for the purpose of obtaining a desired physiological effect—typically elimination of worms, eggs, and lesions from the female genital tract. The effect may be complete or partial, although a complete elimination is the desired end. However, a reduction in symptoms is also a desirable effect. The effect may also be prophylactic, particularly if it lowers the likelihood of infection with lethal agents such as HIV/AIDS and human papilloma virus. In general, inhibiting, slowing, or reversing the progression of the infection or substantially ameliorating symptoms is the goal of the treatment.

For delivery to a uterus to treat uterine schistomsomiasis or uterine fibroids related to schistosomiasis, a liquid formulation can be administered via an intrauterine catheter. The vehicle may be sterile water, sterile distilled water, normal saline, buffered saline, buffered aqueous solution, or other suitable liquid. After instillation, the status of the infected organ in the lower female genital tract should be re-evaluated at one, two, three, or four weeks to determine efficacy. If incomplete cure has been effected, re-treatment should be initiated.

The formulations disclosed here can be used in treating a number of parasitic worm infections, beyond *Schistosoma haematobium*. These include other species of *Schistosoma*, such as *S. japonicum, S. mansoni*, as well as clonorchiasis, opisthorchiasis tapeworm, cysticercosis, hydatid disease and other fluke infections. If the infections of other flukes is localized to another body organ, such as the liver, then a different delivery device or method will be used to achieve local delivery to the liver. Such delivery might be transvascular or percutaneous methods that are performed under image guidance, for example.

Formulations may be made in a vehicle that is pharmaceutically acceptable, such as a gel, a jelly, a liquid, a cream, a foam, etc. Preferably the vehicle is biologically inert and water soluble. Additional additives may be used to act as preservatives and antiseptics. In some cases, antibiotics, antifungals, Ivermectin or Malarone may be added in combination with the active praziquantel. It may be desirable to coat the formulation or use different liquids or semi-solids so that a controlled or delayed release is obtained. Methods of achieving a controlled or delayed release are known in the art.

A vaginal delivery system includes without limitations vaginal solutions, capsules, tablets, gels and jellies, foams, etc. for local delivery to the lower female genital system. The formulation may also include diluents, binders, lubricants, disintegrants, fillers, coloring agents, wetting agents, emulsifying agents, buffers, preservatives, liposomes, thickening agents, etc. The formulation may help the active agent to remain at the site of action for sufficient time for efficacy. Methods of achieving a controlled or delayed release are known in the art. A uterine delivery system includes without limitation aqueous solutions, including normal saline.

Kits are typically containers of more than one component in a single package. The package may be a carton or box, for example. It may contain separately packaged components. Components may also be in a temporarily separate condition which by action of a user may become mixed, typically in a single vessel. Components may be in separate vessels or packages within the kit. Components may be within a divided container that keeps the components separate. Additional components such as instructions, empty vessels, mixing tools may also be in the kit. Typically the more than one components of the kit are intended to be used together, even if not intimately mixed.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Praziquantel powder (600 mg) was mixed with 2.5 g of K-Y™ Jelly (Ingredients: Water, Glycerin, Hydroxyethylcellulose, Chlorhexidine, Gluconate, Gluconolactone, Methylparaben, Sodium Hydroxide.). A plastic vaginal applicator was loaded with the mixture for delivery to the subject. The mixture could include any vaginal lubrication as a medium, such as a jelly, gel, foam, or a liquid. Preferably the medium is water soluble. The ingredients can be mixed by mechanical mixer or by hand to achieve a relatively homogeneous mixture.

Example 2

Shistosomiasis is a blood-borne worm and generally resides in the circulatory system. We found that we are able to cure infected females with FGS of schistosomiasis in the blood but not the vaginal cavity.

A blood sample from a female with FGS was initially tested using Schisto POC-CCA™ from ICT and confirmed to have a blood-borne infection of schistosomiasis. The female with FGS was then treated with three doses of 20 mg/kg oral praziquantel. After two weeks, blood of the female subject was retested and was found to be negative for schistosomiasis. However, observation of a vaginal sample from brushing with a swab was spread on microscope slides showed vaginal cells, fluid, blood, and live schistosomiasis worms still in the vagina.

A single dose of Praziquantel as described in Example 1 was vaginally inserted into the female subject. After two weeks, slides were observed under the microscope to be negative for schistosomiasis worms.

Example 3

Praziquantel powder (1200 mg) is mixed with 20 ml normal saline (0.09% sodium chloride) and inserted using an intrauterine catheter. Mechanical or hand mixing of the ingredients is used to achieve a thorough combination of the ingredients, preferably dissolution.

CLAUSES

1. A unit dosage form of praziquantel, selected from the group consisting of:
   400-1000 mg praziquantel per 1.5-4.5 g vaginal vehicle;
   800-1500 mg praziquantel per 3-7 g vaginal vehicle;
   100-500 mg praziquantel per 1.5-4.5 g vaginal vehicle; or
   800-1500 mg praziquantel per 15-25 ml normal saline uterine vehicle.
2. The unit dosage form of praziquantel of clause 1 wherein the vaginal vehicle is a cream, film, gel, or foam.
3. A kit for locally treating female genital tissue infected with schistosomes, comprising:
   a vaginal applicator; and
   praziquantel.
4. The kit of clause 3 further comprising a water soluble vehicle.
5. The kit of clause 4 wherein the vaginal vehicle is a cream, film, gel, or foam.
6. The kit of clause 4 wherein the praziquantel and the vehicle are premixed.
7. The kit of clause 4 wherein the praziquantel and the vehicle are preloaded in the vaginal applicator.
8. The kit of clause 4 further comprising a mixing vessel or mixing tool for mixing the praziquantel and the vehicle.
9. The kit of clause 3 wherein the praziquantel is preloaded in the vaginal applicator.
10. A kit for locally treating uterine tissue infected with schistosomes, comprising:
    an intrauterine catheter;
    normal saline; and
    praziquantel.
11. The kit of clause 10 wherein the praziquantel and the normal saline are premixed.
12. The kit of clause 11 wherein the praziquantel and the normal saline are preloaded in the vaginal applicator.
13. The kit of clause 10 further comprising a mixing vessel or mixing tool for mixing the praziquantel and the normal saline.

REFERENCES

The disclosure of each reference cited is expressly incorporated herein.
1. "Female Genital Schistosomiasis, a pocket atlas for clinical health-care professionals," World Health Organization, on line reference available at the domain apps.who.int/ and the subdomain iris/bitstream/handle/10665/180863/9789241509299_eng.pdf;jsessionid=2E55C8D3FDE6E3C09C168C402D8BF80E?sequence=1
2. Hotez et al., "Female genital schistosomiasis and HIV/AIDS: reversing the neglect of girls and women," PLOS Neglected Tropical Diseases, (2019) domain doi.org/10.137 and subdomain journal.pntd.0007025
3. U.S. Pat. No. 10,391,134
4. U.S. Pat. No. 10,201,576
5. U.S. Pat. No. 10,555,900
6. U.S. Pat. No. 10,350,042
7. U.S. Pat. No. 9,333,329
8. U.S. Pat. No. 8,840,869
9. U.S. Pat. No. 8,461,115

The invention claimed is:
1. A method of treating genital schistosomiasis in a female patient, comprising:
   inserting and depositing an effective dose of praziquantel into the vaginal cavity of the female patient.
2. The method of claim 1 wherein the praziquantel is in a pharmaceutically acceptable vehicle.
3. The method of claim 2 wherein the vehicle is a cream, film, gel, or foam.
4. The method of claim 1 wherein the praziquantel is in the form of a suppository.
5. The method of claim 2 wherein the vehicle is a gel.
6. The method of claim 1 wherein said inserting and depositing employs an intravaginal applicator.
7. The method of claim 1 further comprising the step of monitoring the vaginal cavity for live schistosome worms, lesions caused by live schistosome worms, or both.
8. The method of claim 7 wherein the monitoring employs a device selected from the group consisting of a digital camera, a colposcope, and a microscope.
9. The method of claim 7 wherein the lesions are grainy sandy patches.
10. The method of claim 7 wherein the lesions are rubbery papules.
11. The method of claim 1 wherein the effective dose is between about 200 to 1,000 mg.
12. The method of claim 1 wherein the effective dose is between about 500-700 mg.
13. The method of claim 7 wherein the monitoring is performed at about 1 week post-treatment.
14. The method of claim 7 wherein the monitoring is performed at about 2 weeks post-treatment.
15. The method of claim 3 wherein the vehicle is water soluble.
16. The method of claim 14 wherein a second round of treatment comprising said inserting and depositing is initiated if live schistosome worms or lesions caused by live schistosome worms are detected at 2 weeks post-treatment.
17. The method of claim 1 further comprising treating the patient with oral praziquantel.
18. The method of claim 17 wherein the oral and the vaginal treatments are performed on different days.
19. A method of treating uterine schistosomiasis or uterine fibroids related to schistosomiasis in a female patient, comprising:
   inserting an intrauterine catheter into the uterus and delivering an effective dose of an aqueous solution of praziquantel via the intrauterine catheter to the uterus.
20. The method of claim 19 further comprising the step of:
   assessing condition of the uterus post-treatment and re-treating if live schistosome worms or uterine fibroids related to schistosomiasis remain after 2 weeks.
21. The method of claim 19 wherein the aqueous solution is a 0.9% saline solution.
22. The method of claim 19 wherein 1,000-1,500 mg of praziquantel is delivered per dose.
23. The method of claim 19 further comprising treating the patient with oral praziquantel.
24. The method of claim 23 wherein the oral and the uterine treatments are performed on different days.
25. The method of claim 1 wherein the praziquantel is combined with ivermectin.
26. The method of claim 5 wherein the praziquantel is combined with ivermectin.
27. The method of claim 19 wherein the praziquantel is combined with ivermectin.
28. An intrauterine catheter comprising an effective dose of an aqueous solution of praziquantel for delivery via the intrauterine catheter to the uterus.
29. The intrauterine catheter of claim 28 further comprising ivermectin.

* * * * *